(12) United States Patent
Chen et al.

(10) Patent No.: US 10,358,807 B2
(45) Date of Patent: Jul. 23, 2019

(54) SUCTION SEAT FOR INTELLIGENT NURSING TOILET BOWL

(71) Applicant: Shandong CRRC Huateng Environment Co., LTD., Jinan, Shandong (CN)

(72) Inventors: Guodong Chen, Jinan (CN); Jianjun Li, Jinan (CN); Baozhen Wang, Jinan (CN); Yongchao Tang, Jinan (CN); Jinxia Zheng, Jinan (CN); Zhe Xing, Jinan (CN); Jinkan Yan, Jinan (CN); Kai Qu, Jinan (CN)

(73) Assignee: SHANDONG CRRC HUATENG ENVIRONMENT CO., LTD., Jinan (CN)

( * ) Notice: Subject to any disclaimer, the term of this patent is extended or adjusted under 35 U.S.C. 154(b) by 0 days.

(21) Appl. No.: 15/529,954

(22) PCT Filed: Dec. 2, 2014

(86) PCT No.: PCT/CN2014/092806
§ 371 (c)(1),
(2) Date: May 25, 2017

(87) PCT Pub. No.: WO2016/082233
PCT Pub. Date: Jun. 2, 2016

(65) Prior Publication Data
US 2018/0202139 A1    Jul. 19, 2018

(30) Foreign Application Priority Data

Nov. 25, 2014   (CN) .......................... 2014 1 0689736
Nov. 25, 2014   (CN) ..................... 2014 2 0719141 U

(51) Int. Cl.
*E03D 9/08*     (2006.01)
*A61F 5/451*    (2006.01)
(Continued)

(52) U.S. Cl.
CPC ............... *E03D 9/08* (2013.01); *A47K 10/48* (2013.01); *A61F 5/451* (2013.01); *A61G 9/00* (2013.01);
(Continued)

(58) Field of Classification Search
CPC .......... A61F 5/451; A61F 5/453; A61F 5/455; A61G 9/00; A61G 9/006; E03D 9/08
See application file for complete search history.

(56) References Cited

U.S. PATENT DOCUMENTS 4,791,686 A * 12/1988 Taniguchi ................ A61G 7/02
                                                 239/588
5,681,297 A * 10/1997 Hashimoto ............. A61F 5/451
                                                 119/164
(Continued)

FOREIGN PATENT DOCUMENTS

CN          1953725 A      4/2007
CN        201073399 Y      6/2008
(Continued)

OTHER PUBLICATIONS

Sep. 9, 2015 Search Report issued in International Application No. PCT/CN2014/092806.
(Continued)

*Primary Examiner* — Janie M Loeppke
(74) *Attorney, Agent, or Firm* — Oliff PLC

(57) ABSTRACT

The invention discloses a suction seat for an intelligent nursing toilet bowl. The suction seat comprises a housing installed on a base, the interior of the housing is an inner cavity, a temperature and humidity sensor, an excrement sensor and a flushing nozzle are respectively installed in the cavity body of the inner cavity, a urine sensor is arranged on the outer side of the lower part of the cavity body, and a discharge port connected with an external negative pressure (Continued)

pipeline is vertically formed in the bottom of the cavity body; and a cleaning device and a ventilation device which are communicated with the interior of the cavity body are arranged on the outer side of the rear part of the cavity body. The cleaning device can automatically adjust the height of the nozzle as well as the pressure and flow rate of running water, thereby realizing overall cleaning on human hip, and overcoming the defects that the existing nozzle is fixed and the flushing area cannot be adjusted. Since the temperature and humidity sensor is arranged inside the suction seat, optimal skin comfort is achieved by adjusting air parameters under the circumstance that neither excrement nor urine is generated. The whole suction seat is compact in structure, and high cleanness of the inner cavity is kept after long-term use; and the whole suction seat adopting the structural design conforming to ergonomics achieves an optimal using effect.

9 Claims, 4 Drawing Sheets

(51) Int. Cl.
<table>
<tr><td>A61G 9/00</td><td>(2006.01)</td></tr>
<tr><td>A47K 10/48</td><td>(2006.01)</td></tr>
<tr><td>E03D 3/00</td><td>(2006.01)</td></tr>
<tr><td>E03D 9/05</td><td>(2006.01)</td></tr>
<tr><td>E03D 11/02</td><td>(2006.01)</td></tr>
<tr><td>E03D 5/10</td><td>(2006.01)</td></tr>
<tr><td>A61G 7/02</td><td>(2006.01)</td></tr>
</table>

(52) U.S. Cl.
CPC ............... *E03D 3/00* (2013.01); *E03D 9/05* (2013.01); *E03D 11/02* (2013.01); *E03D 11/025* (2013.01); *A61G 7/02* (2013.01); *E03D 5/105* (2013.01)

(56) References Cited

U.S. PATENT DOCUMENTS

<table>
<tr><td>6,394,988 B1*</td><td>5/2002</td><td>Hashimoto</td><td>A61F 13/84<br>604/327</td></tr>
<tr><td>2009/0193573 A1*</td><td>8/2009</td><td>Nakamura</td><td>A61G 7/02<br>4/320</td></tr>
<tr><td>2013/0158489 A1*</td><td>6/2013</td><td>Ying</td><td>A61F 5/451<br>604/355</td></tr>
<tr><td>2015/0328072 A1*</td><td>11/2015</td><td>Saitoh</td><td>A61F 5/451<br>4/457</td></tr>
<tr><td>2016/0136338 A1*</td><td>5/2016</td><td>Lee</td><td>A61M 3/06<br>604/319</td></tr>
</table>

FOREIGN PATENT DOCUMENTS

<table>
<tr><td>CN</td><td>101502461 A</td><td>8/2009</td></tr>
<tr><td>CN</td><td>102920565 A</td><td>2/2013</td></tr>
<tr><td>CN</td><td>103655094 A</td><td>3/2014</td></tr>
<tr><td>CN</td><td>103750939 A</td><td>4/2014</td></tr>
<tr><td>CN</td><td>103989563 A</td><td>8/2014</td></tr>
<tr><td>JP</td><td>2009-142384 A</td><td>7/2009</td></tr>
</table>

OTHER PUBLICATIONS

Sep. 9, 2015 Written Opinion issued in International Application No. PCT/CN2014/092806.

* cited by examiner

SUCTION SEAT FOR INTELLIGENT NURSING TOILET BOWL

FIELD OF THE INVENTION

The present invention belongs to the field of home nursing equipment, and relates to a suction seat for an intelligent nursing toilet bowl.

BACKGROUND OF THE INVENTION

At present, as the global aging problem is increasingly prominent and the nursing idea is changed, how to solve the gatism problem of patients has become increasingly difficult. When excrement of bed-ridden or inconvenienced patients, e.g., old people, paralyzed people, severe infectious patients, human vegetables, retardates, gatism patients, etc., is not cleaned timely, harmful effects such as dirt of clothing and bedding, peculiar smell in rooms, private infection and the like are prone to occur, which not only brings unspeakable pain and depression to the patients, but also brings huge economic pressure and psychological burden to nursing staffs. Thus, to develop an intelligent nursing machine capable of sucking excrement and urine, filtering air, removing odor and cleaning privates with warm water is significant for improving the nursing effect, reducing the nursing cost and relieving the mental stress of the patients and the nursing staffs.

After nearly a decade of exploration and development, the present technologically-mature intelligent nursing machine manufacturers include Angelwg, Curaco and Evercare from Korea, SanYo from Japan, Rizhao Xuri and Zhejiang Knight from China, etc. These products all adopt the structural form of a suction seat and a main unit, but face the dilemma of low marketization degree. Among the reasons, the main one is poor overall performance of a key component, i.e., the suction seat, of the nursing machine, embodied in: incomplete cleaning, easily causing dirt residue on the hip; incomplete flushing, easily causing dirt residue in the cavity body of the suction seat and odor emission; poor comfort, easily causing discomfort due to too high skin humidity of human hip; and incomplete sterilization, easily causing bacteria breeding at human privates, etc.

Chinese patent applications CN102920565A and CN103655094A respectively disclose an intelligent/automatic nursing toilet bowl system, including a defecation receiving assembly, a toilet bowl main unit assembly and a connecting pipeline assembly, wherein the connecting pipeline assembly includes a cleaning pipeline, a blow-off pipeline, a vacuum pipeline and an electrical pipeline; the defecation receiving assembly includes a drying device, a flushing device, a defecation receiving device and a detection device, the drying device and the flushing device are arranged above the defecation receiving assembly, and the detection device is arranged in the defecation receiving assembly; the toilet bowl main unit assembly includes a dirt box, a cleaning water unit, a vacuum control unit and a control unit; the detection device, the cleaning water unit and the vacuum control unit are connected with the control unit respectively through the electrical pipeline; the defecation receiving assembly is connected with the dirt box through the blow-off pipeline on one hand and connected with the vacuum control unit and the cleaning water unit respectively on the other hand; and the flushing device is connected with the cleaning water unit through the cleaning pipeline, the drying device is connected with the vacuum control unit through the vacuum pipeline, and the dirt box is connected with the vacuum control unit.

In the intelligent/automatic nursing toilet bowl system respectively disclosed by Chinese patent applications CN102920565A and CN103655094A, when the toilet bowl receiving assembly fixed behind human hip is used for a long term, it has the following defects: 1) the defecation position is different due to users of different genders, ages and the like, so the flushing position is different; the flushing position and area cannot be adjusted by the toilet bowl receiving assembly in the two patents above, thus easily causing incomplete cleaning on the privates of users and dirt residue; and 2) after the receiving assembly contacts the human body, a closed cavity will be formed, and simultaneously, the skin of the hip is exposed in the cavity for a long term; breeding of local bacteria and ulceration of skin are easily caused by too high temperature and humidity, and skin fissures are easily caused by too low temperature and humidity; and the temperature and the humidity cannot effectively be adjusted in the above patents, so that the human skin may feel uncomfortable after long-term use.

Chinese patent application CN103750939A discloses an automatic urinary and fecal nursing device, including a main unit, a feces collector, a directional sliding connector mechanism and a flushing mechanism, wherein the main unit is provided with a dirt storage tank; the directional sliding connector mechanism is used for communicating the dirt storage tank with the feces collector; the feces collector includes a feces collecting trough assembly and a body leaning mechanism, the body leaning mechanism is mounted on a mattress, and the feces collecting trough assembly is mounted on the body leaning mechanism; and the flushing mechanism is arranged in a feces collecting trough of the feces collecting trough assembly.

In the automatic urinary and fecal nursing device disclosed by Chinese patent application CN103750939A, although the adjustable movable flushing mechanism of the feces collector can stretch for cleaning different areas, it cannot automatically adjust the flow rate and the pressure. When the device is used by users of different genders and ages, the too high pressure easily causes discomfort of patients, the too high flow rate easily causes waste of water, whereas the too low pressure and flow rate cannot realize effective flushing.

SUMMARY OF THE INVENTION

An objective of the present invention is to provide a suction seat for an intelligent nursing toilet bowl in order to overcome the above defects of the prior art. A nozzle of the suction seat can automatically adjust the flushing pressure and the flushing height, and thus human privates can be comprehensively cleaned; the suction seat can automatically detect the temperature and humidity of the inner cavity, and can automatically adjust air to dissipate heat so as to achieve good comfort; and the suction seat has a good treatment process and thorough defecation and sterilization effects.

To fulfill the above objective, the present invention adopts the following technical solution:

A suction seat for an intelligent nursing toilet bowl includes a housing installed on a base, the interior of the housing is an inner cavity, a temperature and humidity sensor, an excrement sensor and a flushing nozzle are respectively installed in the cavity body of the inner cavity, a urine sensor is arranged on the outer side of the lower part of the cavity body, and a discharge port connected with an external negative pressure pipeline is vertically formed in the bottom of the cavity body; a cleaning device and a ventilation device which are communicated with the interior of the cavity body are arranged on the outer side of the rear part of the cavity body;

the cleaning device includes a support, a lug with a through hole is arranged at one end of the support, a shunt valve is arranged at the upper part of the support, one end of the shunt valve is connected with a water supply motor controlling the action of the shunt valve, the other end of the shunt valve is communicated with a telescopic barrel, a nozzle communicated with the interior of the telescopic barrel is installed at the other end of the telescopic barrel, the front end of the telescopic barrel penetrates through the through hole of the lug, a hole communicated with the cavity body is formed in the inner cavity opposite to the nozzle, and the hole is opposite to the excretory organ of a human body squatting on the toilet bowl; a driving mechanism installed on the support drives the shunt valve and drives the water supply motor, the telescopic barrel and the nozzle to linearly slide back and forth along the support;

two connectors are arranged outside the shunt valve, one connector is connected with a water inlet pipeline, the other connector is connected with a water outlet pipeline, and the water outlet pipeline is communicated with the flushing nozzle; a valve core inside the shunt valve is of a rotary vane type structure, and is driven by rotation motion of the water supply motor to change the passing sectional area and direction of water flow, thus changing the pressure, flow rate and direction of the water flow; after the shunt valve rotates a set angle range A, clear water flows to the interior of the nozzle via the valve core of the shunt valve and is sprayed out from a nozzle; after the shunt valve continuously rotates to a set range B, clear water flows to the water outlet pipeline via the valve core of the shunt valve, and flows out of the flushing nozzle;

the temperature and humidity sensor, the excrement sensor, the urine sensor, the water supply motor, the driving mechanism and the ventilation device are all controlled by the control system.

The temperature and humidity sensor is installed at the upper part of the cavity body of the inner cavity.

The nozzle is installed in the front of the cavity body of the inner cavity.

Two sides of the shunt valve are clamped on two sides of the support via protruding portions, and each protruding portion is provided with a chute fixedly connected with the driving mechanism.

The telescopic barrel is cylindrical in shape and hollow inside.

The driving mechanism includes a driving motor installed at the bottom of the support, an output shaft of the driving motor is connected with a large roller, a small roller is respectively installed at each of the front and rear ends of the side surface of the support, the small rollers are connected with the large roller by a driving belt to form a closed driving chain, and the driving belt penetrates through the chutes in the protruding portions on the two sides of the shunt valve and is fixed and clamped.

An auxiliary mechanism for adjusting the tightness of the driving belt is further installed on the support, the auxiliary mechanism includes a supporting wheel pressing against the outer side surface of the driving belt, the supporting wheel is installed on the support via a bracket, and a spring having pressing force and used for applying pressure to the supporting wheel is arranged in the bracket.

The ventilation device includes a ventilation pipeline and an air outlet web plate; the air outlet web plate is installed at the upper side part of the cavity body of the inner cavity, the other end of the air outlet web plate is connected with the ventilation pipeline, and the other end of the ventilation pipeline is a reserved port for connection with external air supply equipment.

A jacket is sleeved at the edge of the housing, and is made of flexible and elastic plastic.

In the present invention, the inner cavity is fixed on the base, the cleaning device and the ventilation device are fixed on the outer side of the inner cavity, and the housing covers the cleaning device, the ventilation device and the inner cavity; the lower side of the housing is connected with the base; and the jacket is sleeved at the edge of the housing.

The inner cavity includes a cavity body, a temperature and humidity sensor, an excrement sensor, a urine sensor and a flushing nozzle, wherein the temperature and humidity sensor is installed at the upper part of the inner side of the cavity body, the urine sensor is installed at the lower part of the outer side of the cavity body, and the excrement sensor is installed inside the cavity body. The cavity body is provided with a discharge hole in the lower part, and has one side of a solid structure and the other side completely open; and the discharge port in the lower part needs to be connected with a negative pressure pipeline provided by the outside.

The excrement sensor can detect the existence of liquid or viscous objects and send signals, and is simple and reliable in structure.

The cleaning device includes a water supply motor, a driving motor, a support, a large roller, small rollers, a supporting wheel, a spring, a driving belt, a telescopic barrel, a shunt valve, a nozzle, a water inlet pipeline, a water outlet pipeline, etc., wherein the shunt valve is installed on the support and can slide thereon.

One end of the shunt valve is connected with the water supply motor, the other end of the shunt valve is connected with the telescopic barrel, and the nozzle is installed on the other side of the telescopic barrel. Clear water enters the telescopic barrel via the shunt valve, and then is sprayed out via the nozzle.

The shunt valve provided with chutes outside can linearly slide along the support; two connectors are arranged outside the shunt valve, one connector is connected with the water inlet pipeline, and the other connector is connected with the water outlet pipeline.

A valve body inside the shunt valve is of a rotary vane type structure, and the internal valve core can be driven by external rotation to change the passing sectional area and direction of water flow, thus fulfilling the purpose of changing the pressure, flow rate and direction.

The water supply motor, after being connected with the shunt valve, can drive the valve body inside the shunt valve to rotate forwards and reversely.

After the shunt valve rotates a set angle range A, clear water flows to the interior of the telescopic barrel via the valve core of the shunt valve; after the shunt valve continuously rotates to a set range B, clear water flows to the water outlet pipeline via the valve core of the shunt valve, and then flows out from the flushing nozzle; meanwhile, no matter in which angle range the shunt valve rotates, the flow rate of water flowing through the valve body can be controlled during both the forward rotation and reverse rotation.

The telescopic barrel is cylindrical in shape and hollow inside. The clear water passing through the shunt valve enters the interior of the telescopic barrel, and then is sprayed out by the nozzle.

The driving motor connected with the large roller is used as output power of the driving device; and the driving motor can be controlled by power signals to realize forward and reverse rotation.

The large roller, the small rollers, the supporting wheel and the spring are all installed on the support and connected by the driving belt, wherein the spring is installed between the supporting wheel and the bracket and used for adjusting the tightness of the driving belt to improve the running stability of the system. The driving belt is in non-sliding connection with the shunt valve, so that the driving motor converts rotation motion into linear motion of the shunt valve along the bracket via the large roller, the small rollers, the driving belt, etc.

The ventilation device includes a ventilation pipeline and an air outlet web plate; the air outlet web plate is installed on the side of the inner cavity, the other end of the air outlet web plate is connected with the ventilation pipeline, and the other end of the ventilation pipeline is a reserved port for connection with external air supply equipment.

The flushing nozzle is connected with the water outlet pipeline of the cleaning device.

The housing is in a good streamline shape and conforms to the shape of ergonomics, so that the human private hip where the housing is installed does not feel uncomfortable.

The jacket is made of flexible and elastic plastic, so no adverse reaction is generated after long-term contact of the human body with the jacket; and the jacket is preferably made of high-quality silica gel.

Before working, the jacket needs to be connected with the main unit of the intelligent nursing machine to form a complete system; and the water inlet pipeline, the discharge port of the inner cavity of the suction seat, the ventilation pipeline, the temperature and humidity sensor, the excrement sensor and the urine sensor are all connected with corresponding connectors of the main unit. That is, the main unit needs to provide a temperature adjustable water source, a temperature adjustable air source, a vacuum negative pressure source and a control system, wherein the water source provided by the main unit should have disinfection capability, and simultaneously does not have harm to human skin.

The working process of the present invention is as follows:

The suction seat fixed below human hip is connected with the main unit of the intelligent nursing machine. The nursing process can be divided into a dynamic state and a normal state.

In the dynamic state, after a human body defecates, the excrement sensor detects a signal and then transmits the signal to the main unit. The main unit provides a power signal to control the action of the power supply motor, the power supply motor controls the state of the shunt valve via the rotating angle and drives the valve body of the shunt valve to rotate to a set angle range A, and clear water at the moment enters the telescopic barrel and is sprayed out from the nozzle; meanwhile, the main unit controls the action of the driving motor, and the large roller and the driving belt drive the shunt valve of the cleaning device to reciprocate linearly along the support, thus realizing comprehensive cleaning on human privates. At this moment, the cleaning pressure and the flow rate can be controlled by finely adjusting the rotating angle of the shunt valve automatically or manually. After flushing certain time t1, the water supply motor drives the valve body of the shunt valve to rotate to a set angle range B, the clear water at the moment flows to the flushing nozzle in the cavity body via the pipeline to flush excrement in the cavity body, simultaneously, the main unit provides a negative pressure source, and the dirt is drained away under the actions of the flushing pressure and the negative pressure source. The main unit stops supplying water after certain time t2 and simultaneously provides hot air at a certain temperature to dry human privates, and the main unit stops drying after certain time t3 to complete a cyclic action.

After the human body urinates, the urine sensor detects a signal and then transmits the signal to the main unit. The processing flow is same as above.

In the static state, the parameters including humidity, temperature and the like in the space encircled by the human body and the suction seat are changed over time. The temperature and humidity sensor transmits the parameters to the main unit in real time; after the temperature exceeds a set range (e.g., 20-28° C.), the main unit provides a low-temperature air source, air is blown to human privates after passing through the pipeline and the ventilation web plate, and a reasonable temperature range is finally achieved; after the humidity exceeds a set range (e.g., 40-60%), when the humidity is too high, the main unit provides a dry air source, and air is blown to human privates after passing through the pipeline and the ventilation web plate; and when the humidity is too low, the main unit provides a little clear water, human privates are humidified via the shunt valve and the nozzle, and a reasonable humidity range is finally achieved.

Compared with the prior art, the present invention has the following advantages:

1) The cleaning parameters can be automatically adjusted. By adopting the automatic controllable cleaning device, the height of the flushing nozzle can be automatically adjusted, and the flow rate and pressure of cleaning water can be adjusted, so that human hip is cleaned without dead angles, and the defects that the existing nozzle is fixed and the flushing area cannot be adjusted are overcome.

2) The comfort can be automatically adjusted. Since the temperature and humidity sensor is adopted for detecting the temperature and humidity of the suction seat in real time, air parameters are adjusted by virtue of ventilation, water spraying and other measures under the circumstance that neither excrement nor urine is generated, and the optimal comfort is thus achieved.

3) An optimal using effect is achieved. The suction seat can be often kept in a high clean state by adopting the cleaning water with a disinfection function, and is simple and reliable in structure; by adopting the lower discharge port in the cavity body, the suction seat always keeps little dirt residue under the action of the flushing water having adjustable pressure; and the suction seat adopts the structural design conforming to ergonomics, so that a patient does not feel uncomfortable after long-term use.

in which: 1—base, 2—housing, 3—jacket, 4—inner cavity, 41—cavity body, 42—flushing nozzle, 43—excrement sensor, 44—temperature and humidity sensor, 45—urine sensor, 5—ventilation device, 51—ventilation web plate, 52—air inlet pipe, 6—cleaning device, 61—water inlet pipe, 62—support, 63—telescopic barrel, 64—shunt valve, 641—water inlet, 642—flushing port, 65—water supply motor, 66—small roller, 67—driving belt, 68—large roller, 69—supporting wheel, 70—spring bracket, 71—cleaning nozzle, 72—driving motor.

DETAILED DESCRIPTION OF THE EMBODIMENTS

The present invention will be further described below in combination with the accompanying drawings and embodiments.

Figure 1:
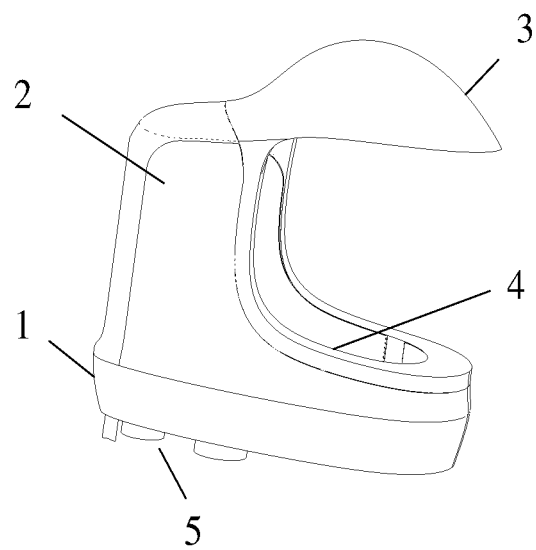
FIG. 1 is a perspective schematic diagram of an embodiment.
Figure 2:
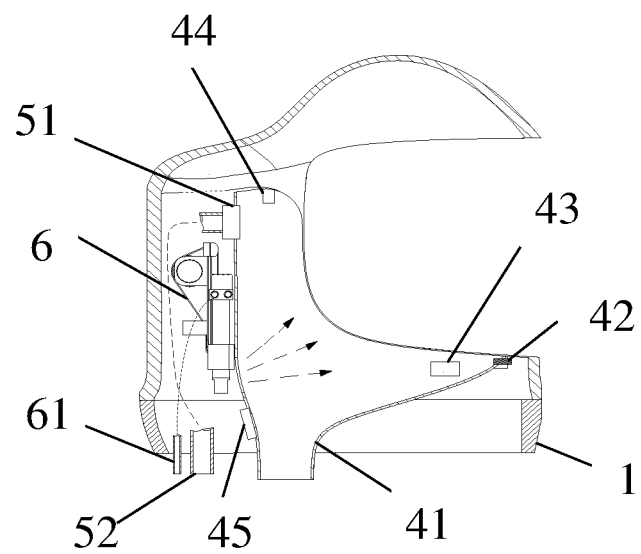
FIG. 2 is a schematic side section view of an embodiment.

As shown in FIGS. 1 and 2, viewed from the outside, the suction seat is mainly composed of a base 1, a housing 2, a jacket 3 and an inner cavity 4, and includes a ventilation device 5 and a cleaning device 6 therein. The base 1 in a specific structure shall be matched with the service environment, and is used for bearing and being fixed with the outside; the housing 2 is a framework structure of the suction seat, and shall conform to the modeling requirement of ergonomics, so that no uncomfortable feel occur after the housing contacts the human skeleton part; and the jacket 3 sleeved at the edge of the housing is a main component in contact with the skin of human hip, and is thus preferably made of elastic plastic having no side effect on the skin.

The housing 2 is installed on the base 1, an inner cavity 4 is formed inside the housing 3, and the inner cavity 4 is mainly composed of a cavity body 41, a flushing nozzle 42, an excrement sensor 43, a temperature and humidity sensor 44 and a urine sensor 45. The temperature and humidity sensor 44, the excrement sensor 43 and the flushing nozzle 42 are respectively installed in the cavity body 41, and the temperature and humidity sensor 44 is installed at the upper part of the cavity body 41. The nozzle 42 is installed in the front of the cavity body 41; the urine sensor 45 is arranged on the outer side of the lower part of the cavity body 41, and a discharge port connected with an external negative pressure pipeline is vertically formed in the bottom of the cavity body 41; the cleaning device 6 and the ventilation device 5 which are communicated with the interior of the cavity body are arranged on the outer side of the rear part of the cavity body. The temperature and humidity sensor 44, the excrement sensor 43, the urine sensor 45, a water supply motor 65, a driving mechanism and the ventilation device 5 are all controlled by a control system.

The discharge port of the cavity body 41 is at the lower part, and this structure avoids accumulation of excrement, is beneficial to discharge of excrement and urine and is beneficial to keeping the inner surface clean after long-term use; the flushing nozzle 42 is preferably of a runner structure having an elliptical section, so that flushing water passing through the flushing nozzle is scattered in a sector manner, and the flushing area is enlarged; and the excrement sensor 43 shall accurately detect excrement with wide signal coverage. The temperature and humidity sensor 44 is mainly used for detecting temperature and humidity of air in the cavity body, so that the system controls the temperature and humidity of air; and the signals of the sensors are all transmitted to a main unit for controlling.

Figure 3:
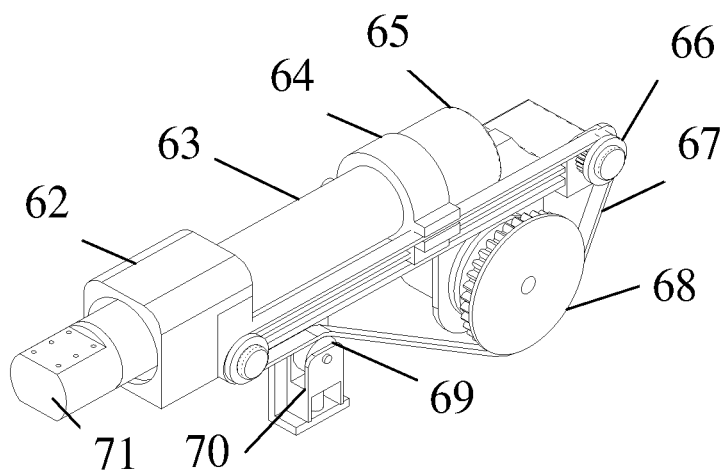
FIG. 3 is a schematic diagram of a structure of a cleaning device in one direction.
Figure 4:
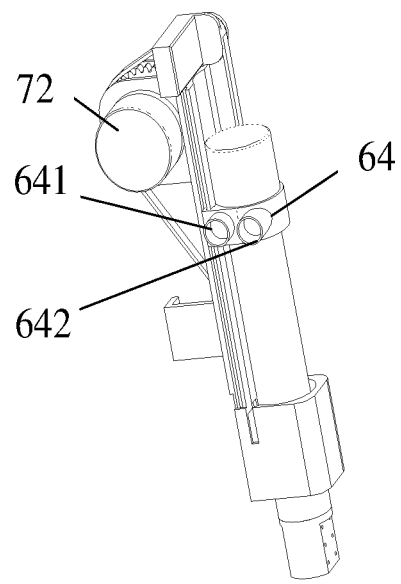
FIG. 4 is a schematic diagram of the structure of the cleaning device in another direction.

As shown in FIGS. 3 and 4, the ventilation device 5 is mainly composed of a ventilation web plate 51 and an air inlet pipe 52. The air outlet web plate 51 is installed at the upside part of the cavity body of the inner cavity, the other end of the air outlet web plate is connected with the ventilation pipeline 52, and the other end of the ventilation pipeline 52 is a reserved port for connection with external air supply equipment.

When the main unit provides an air source, drying air enters the inner cavity 41 via the air inlet pipe 52 and the ventilation web plate 51 to dry the skin of human hip. The cleaning device 6 is mainly composed of a water inlet pipe 61, a support 62, a telescopic barrel 63, a shunt valve 64, a water supply motor 65, small rollers 66, a driving belt 67, a large roller 68, a supporting wheel 69, a spring bracket 70, a cleaning nozzle 71 and a driving motor 72. The small rollers 66, the driving belt 67, the large roller 68, the supporting wheel 69, the spring bracket 70 and the driving motor 72 form a complete driving mechanism, and the driving mechanism is fixed on the support 62; the driving motor 72 is connected with the large roller 68; the driving belt 67 is fixedly connected with the shunt valve 64; the shunt valve 64 can slide linearly along the support 62; and the purpose of this structure is to convert rotation motion of the driving motor 72 into linear motion of the shunt valve 64.

A lug with a through hole is arranged at one end of the support 62, the shunt valve 64 is arranged at the upper part of the support 62, one end of the shunt valve 64 is connected with the water supply motor 65 for controlling the action of the shunt valve 64, the other end of the shunt valve 64 is communicated with the telescopic barrel 63, the cleaning nozzle 71 communicated with the interior of the telescopic barrel is installed at the other end of the telescopic barrel 63, the front end of the telescopic barrel 63 penetrates through the through hole of the lug, a hole communicated with the cavity body is formed in the inner cavity opposite to the nozzle 71, and the hole is opposite to the excretory organ of a human body squatting on the toilet bowl; the driving mechanism installed on the support 62 drives the shunt valve 64 and drives the water supply motor 65, the telescopic barrel 63 and the nozzle 71 to linearly slide back and forth along the support 62.

The shunt valve 64 is a key component of the cleaning device, and is provided with a water inlet 641 and a flushing port 642 at the outer part, wherein the water inlet 641 is connected with the water inlet pipe 61 and used for receiving a water source provided by the main unit; and the flushing port 642 is connected with the flushing nozzle 42 via the water outlet pipe. A valve core inside the shunt valve 64 is of a rotary vane type structure, and is driven by rotation motion of the water supply motor to change the passing sectional area and direction of water flow, thus achieving the purpose of changing the pressure, flow rate and direction. Two sides of the shunt valve 64 are clamped on two sides of the support 62 via protruding portions, and each protruding portion is provided with a chute fixedly connected with the driving mechanism. The telescopic barrel 63 is cylindrical in shape and hollow inside.

The valve core structure inside the shunt valve 64 has functions of adjustable pressure and direction, i.e., when the shunt valve 64 is adjusted to a set angle A, cleaning water sequentially flows through the pipeline 61, the shunt valve 64 and the telescopic barrel 63 and is sprayed out from the cleaning nozzle 71 to clean the skin of human hip; and when the shunt valve is adjusted to a set angle B, cleaning water sequentially flows through the pipeline 61, the shunt valve 64, the flushing port 642 and the flushing nozzle 42 and enters the cavity body 41 to flush excrement and urine. Simultaneously, the shunt valve 64 realizes the function of pressure adjustment via water passing area itself.

The driving mechanism includes the driving motor 72 installed at the bottom of the support 62, an output shaft of the driving motor 72 is connected with the large roller 68, a small roller 68 is respectively installed at each of the front and rear ends of the side surface of the support 62, the small rollers 66 are connected with the large roller 68 by a driving belt 67 to form a closed driving chain, and the driving belt 67 penetrates through the chutes in the protruding portions on the two sides of the shunt valve 64 and is fixed and clamped.

An auxiliary mechanism for adjusting the tightness of the driving belt is further installed on the support 62, the auxiliary mechanism includes a supporting wheel 69 pressing against the outer side surface of the driving belt 67, the supporting wheel 69 is installed on the support 62 via a spring bracket 70, and a spring having pressing force and used for applying pressure to the supporting wheel 69 is arranged in the spring bracket 70.

The cleaning nozzle 71 is connected with the shunt valve 64 via the telescopic barrel 63, the forward and reverse rotation motion of the driving motor 72 is finally converted into linear reciprocating motion of the cleaning nozzle 71, and the height of the discharged water is thus adjusted.

Figure 5:
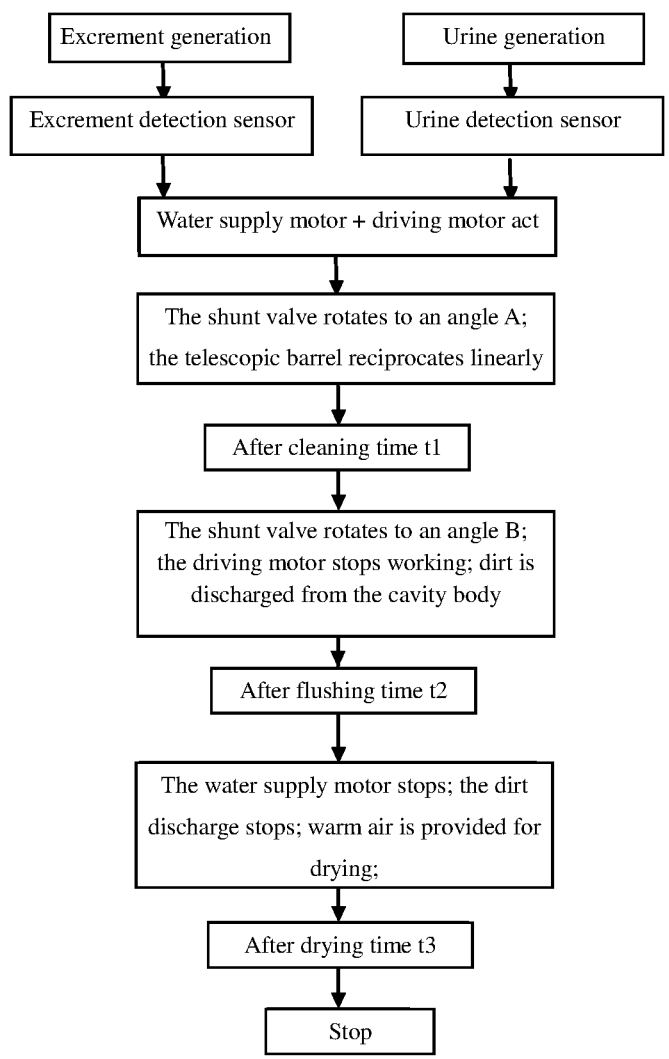
FIG. 5 is a working flow diagram in a dynamic state.
Figure 6:
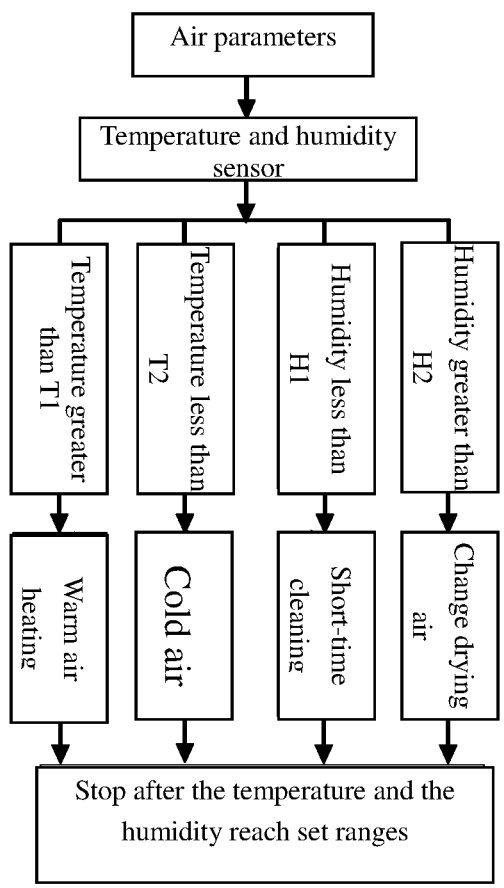
FIG. 6 is a working flow diagram in a static state.

The working flows of the suction seat are shown as FIGS. 5 and 6 and divided into a dynamic working state and a static working state, i.e., when excrement or urine is generated, the suction seat carries out one working flow; and when excrement or urine is not generated but an environmental change is detected, the suction seat carries out the other working flow.

During dynamic working, when a human body defecates or urinates, the excrement sensor 43 and the urine sensor 45 respectively detect a signal, and transmit the signal to the control system of the main unit. Then, the main unit provides a cleaning water source, and controls the actions of the water supply motor 65 and the driving motor 72, wherein the water supply motor 65 drives the valve core of the shunt valve 64 to move, the valve core is adjusted to a preset angle A, the cleaning water at the moment flows through the water inlet pipe 61, the shunt valve 64 and the telescopic barrel 63 and is sprayed out from the cleaning nozzle 71, and the direction of the water flow is shown as arrows; meanwhile, the driving motor 72 drives the shunt valve 64 to move along the support 62 via the large roller 68 and the driving belt 67, the forward and reverse motion of the driving motor 72 is converted into up-and-down motion of the cleaning water nozzle 71, and the cleaned part is completely covered. After a preset time t1, the driving motor 72 stops working; the water supply motor 65 drives the valve core of the shunt valve 64 to move, the valve core is adjusted to a preset angle B, the cleaning water at the moment flows through the water inlet pipe 61, the shunt valve 64 and the flushing nozzle 42 and is sprayed into the cavity body 41 to flush excrement or urine, and dirt is sucked into the main unit under the condition of negative pressure provided by the system. After a preset time t2, the driving motor 72 stops working and stops providing a dirt disposal action, meanwhile the main unit provides warm air, and the warm air passes through the air inlet pipe 52 and the air inlet web plate 51 and is blown into the cavity body 41 to dry human hip. After a preset time t3, the suction seat stops working.

During static working, the control system of the main unit, according to the specific circumstance of a user, can set the air temperature range of the inner cavity, with the maximum not more than T2 and the minimum not less than T1, and set the air humidity range of the inner cavity, with the maximum not more than H2 and the minimum not less than H1. After the temperature and humidity sensor 44 detects air parameters, it judges whether the air parameters are within the set ranges; when the temperature value exceeds T2, the main unit provides cold air to realize cooling via the ventilation device 5; when the temperature value is lower than T1, the main unit provides warm air to realize heating via the ventilation device 5; when the humidity is greater than H2, the main unit provides dry air to realize dehumidification via the ventilation device 5; and when the humidity is less than H2, the main unit provides a little cleaning water to realize humidification via the cleaning device 6; and after the air parameters reach the set values, the main unit stops working.

In specific use, as a part of an intelligent nursing machine, the water inlet pipe 61, the inner cavity 41, the excrement sensor 43, the temperature and humidity sensor 44, the urine sensor 45 and the air inlet pipe 52 of the suction seat are connected with the main unit of the nursing machine, i.e., the main unit provides power signals, control signals, cleaning water, drying air, etc.; the temperatures of the provided drying air and cleaning water are adjustable, and the provided cleaning water shall have a disinfection effect, but does not have harm to the skin after long-term use. After connection, the suction seat is fixed to human hip.

In this structure, because the cleaning water has the disinfection function, other disinfection devices are not needed, and the suction seat is comprehensive in function and simple and reliable in structure.

The description above is merely preferred embodiments of the present invention, and the protection scope of the present invention is not limited thereto. As long as the purposes of the present invention are fulfilled by substantially same means, the means shall fall into the protection scope of the present invention.

The invention claimed is:

1. A suction seat for an intelligent nursing toilet bowl, the suction seat comprising:
 a housing on a base, an interior of the housing including:
  an inner cavity, a temperature and humidity sensor, an excrement sensor, and a flushing nozzle disposed in a cavity body of the inner cavity,
 a urine sensor disposed on an outer side of a lower part of the cavity body;
 a discharge port vertically formed in a bottom of the cavity body and connected to an external negative pressure pipeline;
 a cleaning device and a ventilation device in communication with an interior of the cavity body and disposed on an outer side of a rear part of the cavity body, the cleaning device including:
  a support,
  a lug having a through hole and being disposed at a first end of the support,
  a shunt valve disposed at an upper part of the support, where a first end of the shunt valve is connected to a water supply motor configured to control an action of the shunt valve, a second end of the shunt valve is in communication with a telescopic barrel, a cleaning nozzle is in communication with an interior of the telescopic barrel and is disposed at a second end of the telescopic barrel, a first end of the telescopic barrel penetrates through the through hole of the lug, and
  a driving mechanism disposed on the support that is configured to drive the shunt valve and the water supply motor, the telescopic barrel and the cleaning nozzle being configured to linearly slide along the support;

a hole in communication with the cavity body and formed in the inner cavity on an opposite side with respect to the flushing nozzle; and a first connector and a second connector disposed adjacent to the shunt valve, the first connector being connected with a water inlet pipeline and the second connector being connected with a water outlet pipeline, the water outlet pipeline being in communication with the flushing nozzle, wherein:

the shunt valve includes a valve core having a rotary vane type structure, the valve core being configured to be driven by rotation of the water supply motor such that a pressure, a flow rate, and a direction of water flow through the shunt valve are changed;

the shunt valve is configured such that:

upon the shunt valve rotating a set angle range A, water is to flow to an interior of the cleaning nozzle via the valve core and the water is to be sprayed out from the cleaning nozzle; and upon the shunt valve continuously rotating to a set range B, water is to flow to the water outlet pipeline via the valve core and the water is to flow out of the flushing nozzle; and the temperature and humidity sensor, the excrement sensor, the urine sensor, the water supply motor, the driving mechanism, the ventilation device are all controlled by a controller.

2. The suction seat of claim 1, wherein the temperature and humidity sensor is disposed at an upper part of the cavity body of the inner cavity.

3. The suction seat of claim 1, wherein the flushing nozzle is installed in a front side of the cavity body of the inner cavity.

4. The suction seat of claim 1, wherein opposite sides of the shunt valve are clamped on opposite sides of the support by a plurality of protruding portions, each protruding portion of the plurality of protruding portions includes a chute connected to the driving mechanism.

5. The suction seat of claim 1, wherein the telescopic barrel is cylindrical and hollow.

6. The suction seat of claim 4, wherein the driving mechanism includes:

a driving motor disposed at a bottom side of the support, the driving motor having an output shaft connected to a large roller, and a plurality of small rollers disposed at a front end of a side surface of the support and a rear end of the side surface of the support, the plurality of small rollers being connected to the large roller by a driving belt to form a closed driving chain, the driving belt penetrating through each chute of each protruding portion of the plurality of protruding portions on the opposite sides of the shunt valve.

7. The suction seat of claim 6, further comprising an auxiliary mechanism configured to adjust a tightness of the driving belt, the auxiliary mechanism being disposed on the support and including:

a supporting wheel pressed against an outer side surface of the driving belt, the supporting wheel being disposed on the support via a bracket, and a spring configured to apply pressure to the supporting wheel, the spring being disposed in the bracket.

8. The suction seat of claim 1, wherein the ventilation device includes a ventilation pipeline and an air outlet web plate, a first end of the air outlet web plate being disposed at an upper side part of the cavity body of the inner cavity, a second end of the air outlet web plate being connected to a first end of the ventilation pipeline, and a second end of the ventilation pipeline being configured to connect to external air supply equipment.

9. The suction seat of claim 1, wherein a jacket is disposed at an edge of the housing, the jacket being made of flexible and elastic plastic.

\* \* \* \* \*